United States Patent [19]

Crochemore

[11] 4,151,193

[45] Apr. 24, 1979

[54] PROCESS FOR THE PREPARATION OF ALIPHATIC ISOCYANATES

[75] Inventor: Michel Crochemore, Oullins, France

[73] Assignee: Philagro, Lyons, France

[21] Appl. No.: 859,930

[22] Filed: Dec. 12, 1977

[30] Foreign Application Priority Data

Dec. 27, 1976 [FR] France ................................ 76 39801

[51] Int. Cl.$^2$ ............................................. C07C 118/00
[52] U.S. Cl. .................................................. 260/453 P
[58] Field of Search ....................................... 260/453 P

[56] References Cited

U.S. PATENT DOCUMENTS 3,275,669  9/1966  Ulrich et al. ..................... 260/453 P

OTHER PUBLICATIONS

Hentschel, Berichte, vol. 17, pp. 1284–1289 (1884).

Primary Examiner—Dolph H. Torrence
Attorney, Agent, or Firm—Browdy and Neimark

[57] ABSTRACT

Symmetric ureas are converted to aliphatic isocyanates in high yields by reacting said ureas with phosgene at temperatures of at least 150° C. and in a solvent having a boiling temperature greater than 150° C.

10 Claims, No Drawings

PROCESS FOR THE PREPARATION OF ALIPHATIC ISOCYANATES

The present invention relates to a process for preparing aliphatic or cycloaliphatic isocyanates by phosgenation of symmetric ureas.

Certain symmetric ureas are byproducts of the reaction when chemical compounds usable as active substances in plant health compositions are prepared. This is the case in particular of the NN' dialkylureas, in particular NN' diisopropyl urea obtained when hydantoin 1-(3,5-dichlorophenyl)-3-isopropyl carbamoyl is manufactured.

It is known that aromatic isocyanates, in particular phenyl isocyanates, can be prepared by phosgenation of an aromatic symmetric urea beginning at a temperature of 150° C. (see *Chem. Rev.* 43–203, 1948).

It is also known (see U.S. Pat No. 3,275,669) that isocyanates can be prepared in two stages by cold phosgenation (avoiding too great an excess of phosgene) of symmetric urea, giving allophanyl chloride, followed by thermal decomposition of this compound, preferably dissolved in an inert solvent, into isocyanate whereby hydrochloric acid is given off. Although this process is described as theoretically applicable to aliphatic symmetric ureas, the isocyanate yield differs considerably according to the starting urea. Although yields can be excellent for ureas substituted by linear alkyl radicals, they are poor and even as low as a few percent in cases where the nitrogen atoms are substituted by branched, especially secondary, alkyl radicals such as isopropyl or cyclohexyl.

An explanation for this phenomenon has been proposed according to which, in the case of substituted alkyl radicals, another reaction occurs:

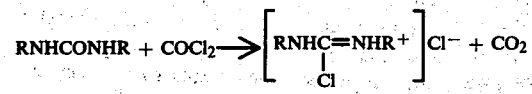

which considerably restricts or even completely prevents isocyanate formation.

Thus, it has not been possible hitherto to obtain aliphatic isocyanates in a single stage with satisfactory yields by phosgenation or the corresponding aliphatic symmetric ureas.

The present invention relates to a process which does not have the aforementioned disadvantages and which consists of preparing aliphatic isocyanates by phosgenation of symmetric ureas, characterized by causing phosgene to react with a disubstituted NN' symmetric urea in a single stage as follows:

In the urea formula, R is an alkyl radical with one to six carbon atoms. This reaction is carried out in solution in a high-boiling inert organic solvent at a temperature of 150° to 350° C.

The R radical is preferably an alkyl radical with one to four carbon atoms or the cyclohexyl radical, the best results being obtained when R is one of the propyl, isopropyl, or butyl radicals.

The phosgene can be introduced into the reaction medium by bubbling in the gaseous state or in the solution form in an organic solvent. In general the isocyanate yield is improved if there is excess phosgene with respect to the substituted urea; the reaction is preferably carried out with a molar phosgene/urea ratio of 1/1 to 3/1.

The solvent usable in the process according to the invention must have a high boiling point, over 150° C., the minimum temperature necessary for the reaction. Examples of suitable organic solvents which can be cited are quinoline, 1-chloronaphthalene, N-methyl caprolactam, and, preferably, sulfolane and paraffin oil. However, this list is not exhaustive and other equivalent solvents can also be used.

According to another essential characteristic of the process, the temperature of the reaction medium must be between 150° and 350° C., approximately, and preferably between 200° and 250° C. The temperature enables the reaction to be started and facilitates it by favoring elimination of the resulting hydrochloric acid as well as distillation of isocyanate. If the reaction is carried out below 150° C., the isocyanate yield is very low, since the starting products combine according to the prior art, principally into either allophanyl chloride or into chloroformamidinium chloride. Above 350° C., on the other hand, the reaction is theoretically possible, but the risk of the urea decomposing by heat increases and the choice of a solvent with a sufficiently high boiling point becomes increasingly narrower.

The heating time is a function of the nature of the urea, that of the solvent, and the phosgene/urea molar ratio. In general, times between 0.5 and 10 hours, preferably between 1.5 and 7 hours, will be used.

The examples hereinbelow illustrate the process according to the invention.

EXAMPLE 1

A 250 ml three-neck flask, equipped with a thermometer, an agitator, a distiller, and a down-coming tube for bubbling in phosgene is charged with 100 ml sulfolane (tetramethylene sulfone with a boiling point of 285° C.) and 14.4 g (i.e., 0.1 mole) diisopropyl urea. The apparatus is then flushed with nitrogen for 10 min. It is heated to 225° C. with the aid of a metal bath, while stirring. The reaction mixture is held at this temperature for 6 hours, while the phosgene is bubbled in at a slow rate regulated by cooling the reservoir. The isocyanate distills slowly. When all the phosgene has passed in a little nitrogen is bubbled through and heating is stopped. The reaction times vary from 4 hours to 5 hours 45 minutes. The hydrochloric acid and excess phosgene given off are trapped in soda and xylene bubblers respectively.

The distillate is assayed to determine the quantity of isocyanate obtained.

The table below gives the yields obtained as a function of the phosgene/urea molar ratio.

Table 1

| Molar ratio $COCl_2$ | Phosgene passage time | % isocyanate/urea yield |
|---|---|---|
| 1 | 5 h 25 m | 42.5 |
| 1.8 | 2 h 45 m | 58.0 |
| 2.2 | 4 h | 68.4 |
| 3 | 4 h 40 m | 65.9 |

EXAMPLE 2

One operates as in Example 1 with different solvents and different phosgene/urea ratios.

The supplementary conditions and results are set down in the table hereinbelow.

Table 2

| Molar ratio COCl2 | Type of solvent | Boiling point | Phosgene passage time | % isocyanate/ urea yield |
|---|---|---|---|---|
| 2 | paraffin oil | 190°–230° C./0.1 mmHg | 5 h | 84.7 |
| 1.15 | quinoline | 237° C. | 3 h | 50 |
| 1.1 | N-methyl caprolactam | 321° C. | 2 h 35 m | 48 |

EXAMPLE 3

One operates as in Example 1 establishing the phosgene/urea molar ratio at 2 and the temperature at 225° C., the solvent being paraffin oil and the time taken for phosgene is made to vary.

This time and the associated yields are given in the table hereinbelow.

Table 3

| Time | % isocyanate/urea yield |
|---|---|
| 0 h 35 m | 48.2 |
| 1 h 55 m | 64.0 |
| 3 h 25 m | 70.8 |
| 5 h | 84.7 |
| 6 h | 84.5 |

EXAMPLE 4

One proceeds as in Example 1, beginning from different NN'-dialkylureas under appropriate conditions. These conditions as well as the associated isocyanate yields are given in the table hereinbelow.

Table 4

| Starting urea R = | COCl2 * | Solvent | Temperature | Phosgene passage time | Isocyanate yield, % |
|---|---|---|---|---|---|
| $CH_3-$ | 2 | chloronaphthalene ** | 240° C. | 2 h 25 m | 44.7 |
| $CH_3CH_2CH_2-$ | 2.4 | chloronaphthalene ** | 250° C. | 3 h 10 m | 88.8 |
| $CH_3(CH_2)_3-$ | 2.6 | chloronaphthalene ** | 225° C. | 1 h 35 m | 72.5 |
| $(CH_3)_3C-$ | 1.5 | paraffin oil | 230° C. | 2 h 15 m | 43.0 |
| cyclohexyl | 2 | paraffin oil | 250° C. | 2 h | 37.0 |
| $CH_3\diagdown CH_3\diagup CH_3$ | 2 | paraffin oil | 225° C. | 1 h 35 m | 64.0 |

\* = molar ratio
\*\* boiling point: 263° C.

EXAMPLE 5

The purpose of this example is to compare the process described in U.S. Pat. No. 3,275,669 (process A) for phosgenating a symmetric urea and the process according to the invention (INV). It should first be noted that the aforementioned process requires two stages for obtaining isocyanate.

The tests were carried out according to the method described in the reference for the known process and according to the method of Example 1 for the process according to the invention. The precise conditions characteristic of each process and the yields obtained are shown in the table hereinbelow. With regard to the known process, the yields are also expressed in isocyanate, it being assumed that the second stage of thermal decomposition of allophanyl chloride into isocyanate was practically quantitative.

Table 5

| Starting urea | COCl2/urea | Solvent | Temperature | Phosgene passage time | % isocyanate/urea yield | Process |
|---|---|---|---|---|---|---|
| diisopropyl urea | 1.8 | Sulfolane | 25° C. | 4 h 15 m | 11.1 | A |
|  | 1.8 | Sulfolane | 225° C. | 5 h 45 m | 58.0 | INV |
| dicyclohexyl urea | 1.1 | Dichloroethylene | 2° C. | 1 h 50 m | 12.5 | A |
|  | 2.0 | Paraffin oil | 250° C. | 2 h | 37.0 | INV |

With regard to the dicyclohexyl urea, it should be pointed out that the phosgene/urea molar ratio is not critical and a ratio on the order of 2 leads to a similar yield.

This table shows clearly that the process according to the invention enables alkylisocyanates to be obtained, particularly those which have a secondary carbon on the nitrogen atom, not only in a single stage instead of two stages with the known process, but with 3 to 5 times the yield.

All the above examples illustrate the essential characteristics of the process according to the invention, namely that it is carried out in a single stage, that it enables alkylated aliphatic isocyanates to be prepared by both linear and branched or cyclic radicals to be prepared, and that the yields can be excellent and clearly superior to those of processes known hitherto using the same starting products.

I claim:

1. A process for manufacturing aliphatic isocyanates by phosgenation of substituted symmetric ureas, comprising reacting phosgene at a temperature between 150° and 350° C. with a disubstituted symmetric NN' urea as follows:

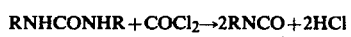

$RNHCONHR + COCl_2 \rightarrow 2RNCO + 2HCl$ in which R is an alkyl radical with 1 to 6 carbon atoms, dissolved in an inert organic solvent with a boiling point more than 150° C.

2. Process according to claim 1, characterized by the R radical being an alkyl radical with 1 to 4 carbon atoms or the cyclohexyl radical.

3. Process according to claim 2, characterized by the R radical being an isopropyl radical.

4. Process according to claim 1, characterized by the phosgene urea molar ratio between 1 and 3.

5. Process according to claim 4, characterized by the phosgene being bubbled into the urea-solvent mixture, in the gaseous state.

6. Process according to claim 4, characterized by the phosgene being added in the form of an organic solution to the organic urea solution.

7. Process according to claim 4, characterized by the reaction being carried out at a temperature of between 200 and 250° C.

8. Process according to claim 4, characterized by the solvent being chosen from the group including paraffin oil, sulfolane, 1-chloronaphthalene, quinoline, and N-methylcaprolactam.

9. Process according to claim 4, characterized by the reaction mixture being heated for 0.5 to 10 hours.

10. Process according to claim 9, characterized by heating being maintained for a length of time equal to 1.5 to 7 hours.

* * * * *